(12) United States Patent
Fardis et al.

(10) Patent No.: US 7,655,623 B2
(45) Date of Patent: Feb. 2, 2010

(54) DAB⁹ DERIVATIVES OF LIPOPEPTIDE ANTIBIOTICS AND METHODS OF MAKING AND USING THE SAME

(75) Inventors: Maria Fardis, San Carlos, CA (US);
Dale R. Cameron, Richmond (CA);
Vincent A. Boyd, Vancouver (CA)

(73) Assignee: Migenix Inc., Vancouver British Columbia (CA)

( * ) Notice: Subject to any disclaimer, the term of this patent is extended or adjusted under 35 U.S.C. 154(b) by 49 days.

(21) Appl. No.: 11/539,139

(22) Filed: Oct. 5, 2006

(65) Prior Publication Data
US 2007/0167357 A1 Jul. 19, 2007

Related U.S. Application Data

(63) Continuation of application No. 10/336,641, filed on Jan. 2, 2003, now Pat. No. 7,125,844.

(60) Provisional application No. 60/453,710, filed on Jan. 3, 2002.

(51) Int. Cl.
*A61K 38/00* (2006.01)
(52) U.S. Cl. .......................................................... 514/9
(58) Field of Classification Search .................. None
See application file for complete search history.

(56) References Cited

U.S. PATENT DOCUMENTS

| | | | |
|---|---|---|---|
| 3,057,779 | A | 10/1962 | Shay et al. |
| 3,160,561 | A | 12/1964 | Shibata et al. |
| 3,639,582 | A | 2/1972 | Umezawa et al. |
| 3,781,420 | A | 12/1973 | Nishimura et al. |
| 3,817,973 | A | 6/1974 | Bouchaudon et al. |
| 4,524,135 | A | 6/1985 | Abbott et al. |
| 4,977,083 | A | 12/1990 | Boeck |
| 4,994,270 | A | 2/1991 | Boeck et al. |
| 5,028,590 | A | 7/1991 | Fukuda et al. |
| 5,039,789 | A | 8/1991 | Fukuda et al. |
| 5,629,288 | A | 5/1997 | Lattrell et al. |
| 5,912,226 | A | 6/1999 | Baker et al. |
| 6,146,872 | A | 11/2000 | Ueda et al. |
| 6,194,383 | B1 | 2/2001 | Hammann et al. |
| 6,716,962 | B2 | 4/2004 | Borders et al. |
| 7,125,844 | B2 * | 10/2006 | Fardis et al. .................. 514/9 |
| 2002/0028771 | A1 | 3/2002 | Curran et al. |

FOREIGN PATENT DOCUMENTS

| | | |
|---|---|---|
| EP | 629636 | 12/1994 |
| WO | WO-9943700 | 9/1999 |
| WO | WO-0205837 | 1/2002 |

OTHER PUBLICATIONS

Vertesy, et al "Friulimicins: Novel Lipopeptide Antibiotics with Peptidoglycan Synthesis Inhibiting Activity from Actinoplanes friuliensissp. nov. II. Isolation and Structural Characterization," The Journal of Antibiotics 53(8): 816-827, Aug. 2000. Cited by examiner.
Bodanszky, M. et al., "Structure of the Peptide Antibiotic Amphomycin," Journal of the American Chemical Society 95(7): 2352-2357, Apr. 4, 1973. cited by other.
Boeck, L.D. et al., "Deacylation of A21978C, an Acidic Lipopeptide Antibiotic Complex, By Actinoplanes utahensis," The Journal of Antibiotics 41(8): 1085-1092, Aug. 1988. cited by other.
Debono, M. et al., "Enzymatic and Chemical Modifications of Lipopeptide Antibiotic A21978C: The Synthesis and Evaluation of Daptomycim (LY146032)," The Journal of Antibiotics 41(8): 1093-1105, Aug. 1988. cite- d by other.
Fujino, M., "On Glumamycin, a New Antibiotic. VI. An Approach to the Amino Acid Sequence," Bulletin of the Chemical Society of Japan 38(4): 517-522, 1965. cited by other.
Hausmann, W.K. et al., "Structure Determination of Fatty Acids from the Antibiotic Aspartocin," in Antimicrobial Agents and Chemotherapy—1963, Proceeding of the Third Interscience Conference on Antimicrobial Agents and Chemotherapy, Sylvester, J.C.(ed. ), American Society for Microbiology, 1963, pp. 352-359. cited by other.
Hausmann, W.K. et al., ".alpha., .beta.-Diaminobutyric Acid Obtained from Aspartocin," The Journal of Antibiotics 22(5): 207-210, May 1969. cited by other.
Heinemann, B. et al., "Amphomycin, A New Antibiotic," Antibiotics and Chemotherapy 3: 1239-1242, 1953. cited by other.
Hinuma, Y., "Zaomycin, A New Antibiotic from a *Streptomyces* sp.," The Journal of Antibiotics, Ser. A 7(4): 134-136, Aug. 1954. cited by other.
Huber, F.M. et al., "The formation of daptomycin by supplying decanoic acid to *Strptomyces* roseosporus cultures producing the antibiotice complex A21978C," Journal of Biotechnology 7(4): 283-292, 1988. cited by other.
Martin and Hausmann, "Isolation and Identification of D-.sub..alpha.-Pepecolic Acid, .alpha.[L],.beta.-Methylaspartic Acid and .alpha.,.beta.-Diaminobutyric Acid from the Polypeptide Antibiotic Aspartocin," Journal of the American Chemical Society82: 2079, Apr. 20, 1960. cited by other.
Naganawa, H. et al., "A Novel Fatty Acid from Laspartomycin," The Journal of Antibiotics 23(8): 423-424, Aug. 1970. cited by other.
Naganawa, H. et al., "Laspartomycin, A New Anti-Staphylococcal Peptide," The Journal of Antibiotics 21(1): 55-62, Jan. 1968. cited by other.
Shay, A.J. et al., "Aspartocin. I. Production, Isolation, and Characteristics," Antibiotics Annual 1959-1960, pp. 194-198. cited by other.
Shoji, J-I et al., "Studies on Tsushimycin. I. Isolation and Characterization of an acidic acylpeptide containing a new fatty acid," The Journal of Antibiotics 21(7): 439-443, Jul. 1968. cited by other.
Vertesy, L. et al., "Friulimicins: Novel Lipopeptide Antibiotics with Peptidoglycan Synthesis Inhibiting Activity from Actinoplanes friuliensis sp. nov. II. Isolation and Structural Characterization," The Journal of Antibiotics 53(8): 816-827, Aug. 2000. cited by other.

* cited by examiner

*Primary Examiner*—Cecilia Tsang
*Assistant Examiner*—Thomas S Heard
(74) *Attorney, Agent, or Firm*—Darby & Darby P.C.

(57) ABSTRACT

The present invention provides Dab⁹ derivatives of amphomycin-type lipopepetide antibiotics that display antimicrobial activity against Gram-positive bacteria, methods and intermediates for synthesizing the compounds and methods of using the compounds in a variety of contexts, including in the treatment and prevention of infections.

8 Claims, 1 Drawing Sheet

FIG. 1

DAB⁹ DERIVATIVES OF LIPOPEPTIDE ANTIBIOTICS AND METHODS OF MAKING AND USING THE SAME

CROSS-REFERENCE TO RELATED APPLICATIONS

This application is a continuation of U.S. application Ser. No. 10/336,641, filed Jan. 2, 2003, now allowed; which application claims the benefit of U.S. Provisional Application No. 60/453,710, filed Jan. 3, 2002, which applications are incorporated by reference in their entirety.

1. FIELD OF THE INVENTION

The present invention relates generally to derivatives of lipopeptide antibiotics of the amphomycin type, methods and intermediates for their preparation and methods for their use as pharmacologically active substances, in particular against infections caused by Gram-positive bacteria.

2. BACKGROUND OF THE INVENTION

Secondary metabolites from microorganisms are successfully employed for the treatment of infectious diseases. Secondary metabolites are low molecular weight compounds produced by "biosynthetic one-way streets" which branch off from the primary metabolism. The function of the secondary metabolites for the particular producer is unclear. To date, about 8000 secondary metabolites isolated from cultures of various microorganisms (especially fungi and bacteria of the genus *Streptomyces*) are known.

These secondary metabolites are mainly used to treat infectious diseases. One important class of such secondary metabolites are the amphomycin-type lipopeptide antibiotics. The amphomycin-type lipopeptide antibiotics display their antibiotic activity against Gram-positive bacteria, such as, for example, Strepto-, Staphylo- and Enterococci and consist of a macrocyclic peptide "core" acylated at its N-terminus with a lipophilic fatty acid. The amphomycin-type antibiotics are generally produced as mixtures of compounds that differ with respect to the structures of their macrocyclic peptide cores and/or their fatty acid moieties. Examples of such amphomycin-type lipopeptide antibiotics include: amphomycin (glumamycin) Heinemann et al., 1953, *Antibiot. Chemother.* 3:1239-1242; Fujino et al., 1965, *Bull. Chem. Soc. Jap.* 38:515; Bodanszky et al., 1973, *J. Am. Chem. Soc.* 95:2352; Shibata et al., U.S. Pat. No. 3,160,561); aspartocin (Shay et al., U.S. Pat. No. 3,057,779; Shay et al., 1960, *Antibiotics Ann.* 194; Hausman et al., 1964, *Antimicrob. Ag. Chemother.* 352; Hausman et al., 1969, *J. Antibiotics* 22:207; Martin et al., 1960, *J. Am. Chem. Soc.* 2079); crystallomycin (Gauze et al., 1957, *Antibiotiki* 2:9-14); antibiotic A1437 (Hammann et al., EP 0 629 636 B1; Hammann et al., U.S. Pat. No. 6,194,383; Lattrell et al., U.S. Pat. No. 5,629,288); friulimycin (Vertesy et al., 2000, *J. Antibiotics* 53:816); tsushimycin (Shoji et al., 1968, *J. Antibiotics* 21:439; Nishimura et al., U.S. Pat. No. 3,781,420); and zaomycin (Hinuma, 1954, *J. Antibiotics* 7(4): 134-136; Kuroya, 1960, *Antibiotics Ann.* 194; Kuroya, JP 8150).

Owing in part to the wide-spread use of antibiotic therapies, many strains of bacteria have developed resistance to these and other classes of antibiotic compounds. Strains of the genera *Strepto-*, *Staphylo-* and *Enterococcus* are proving to be particularly problematic organisms to control efficiently because of developed resistance to conventional antibiotics (for example β-lactam antibiotics and/or glycopeptide antibiotics such as, for example, vancomycin and teicoplanin). Another group of microorganism strains that have developed resistance include the methicillin-resistant *Staphylococcus aureus* strains ("MRSA" strains). It is now known that these MRSA strains are often resistance to other antibiotics (for example quinolones) in addition to methicillin. Given the rampant rise of strains of microorganisms that are resistant to current antibiotic therapies, there is a continuous need for the development of novel antibiotics and antibiotics with novel mechanisms of action.

3. SUMMARY OF THE INVENTION

In one aspect, the present invention provides novel lipopeptide antibiotics of the amphomycin type. The novel antibiotics consist of an amphomycin-type macrocyclic peptide "core" and a lipophilic fatty acid moiety. The macrocyclic peptide core includes a Dab residue, or other amino acid having a side chain with a primary amine group, which is typically at the 9-position of the macrocycle ("Dab⁹ residue"). The macrocyclic peptide core also includes an exocyclic amino acid, which is typically Asp or Asn, which intervenes the cyclic portion of the core and the lipophilic fatty acid moiety. The β-amino group of the macrocyclic Dab⁹ residue is acylated with a substituent that includes a primary or secondary amine. In one embodiment, this amine-containing substituent is an amino acid, typically an α-, β- or γ-amino acid. The amino acid may optionally include one or more side-chain moieties, for example, a side chain of one of the twenty genetically encoded amino acids. The lipophilic fatty acid moiety is linked to the N-terminus of the macrocyclic peptide core via its terminal carboxyl group. The lipophilic fatty acid moiety may be a linear or branched, saturated or singly or multiply unsaturated fatty acid or hydroxy fatty acid with a chain length of from 6 to 22 carbon atoms. As will be described in more detail in connection with methods of synthesizing the compounds, the compounds of the invention may be structurally pure, or they may be in the form of a composition comprising a mixture of one or more structurally different compounds. They may also be in the form of free acids or bases or in the form of salts, such as pharmaceutically-acceptable salts.

In another aspect, the present invention provides compositions comprising the compounds of the invention. Generally, the compositions comprise one or more compounds of the invention and an appropriate carrier, excipient or diluent. The exact nature of the carrier, excipient or diluent will depend upon the desired use for the composition, and may range from being suitable or acceptable for environmental uses, to being suitable or acceptable for veterinary uses, to being suitable or acceptable for human use.

In still another aspect, the present invention provides methods of synthesizing the compounds of the invention. In one embodiment, the compounds of the invention may be prepared from a parent amphomycin-type lipopeptide antibiotic isolated from culture by reacting the parent antibiotic with an appropriately protected reagent, such as an appropriately protected amino acid, under conditions suitable for attaching the reagent to the β-nitrogen of the macrocyclic Dab⁹ residue. Any protecting groups present may then be removed to yield a Dab⁹ derivative of the invention.

Typically, such parent antibiotics are mixtures of compounds that differ from one another with respect to the structures of their macrocyclic peptide cores and/or fatty acid moieties. In this instance, the resultant Dab⁹ derivatives of the invention are obtained as mixtures of compounds, the structures and relative quantities of which are dictated by the structures and relative quantities of the compounds comprising the parent antibiotic mixture. When structurally pure compounds of the invention are desired, the component compounds comprising the parent antibiotic mixture may be separated and isolated from one another before derivatization of the macrocyclic $Dab^9$ residue. Alternatively, the separation and isolation may be carried out on the resultant product of the $Dab^9$ derivatization reaction, either before or after removal of any protecting groups, to yield structurally pure $Dab^9$ derivatives of the invention.

In many cases, the structures of the fatty acid moieties of the parent antibiotics are unknown. $Dab^9$ derivatives of the invention having precisely defined fatty acids may be obtained by removing the lipophilic fatty acid moiety and replacing it with a fatty acid having a specified structure. In one embodiment, the parent antibiotic mixture is delipidated to yield a delipidated intermediate and this delipidated intermediate is then reacted with the desired fatty acid under acylating conditions to yield a synthetic antibiotic having a precisely defined fatty acid moiety. This synthetic antibiotic may then be derivatized according to the methods described above to yield $Dab^9$ derivatives of the invention. As will be recognized by skilled artisans, the β-amino group of the macrocyclic $Dab^9$ residue should be protected with a suitable protecting group prior to delipidation of the parent antibiotic.

In instances where all of the component compounds of the particular parent antibiotic mixture share the same macrocyclic peptide core, and differ in structure only with respect to the structures of their fatty acid moieties, structurally pure $Dab^9$ derivatives having a specified fatty acid moiety are obtained. In instances where the component compounds of the parent antibiotic mixture have structurally distinct macrocyclic peptide cores, such as is the case for, e.g., antibiotic A1437, the resultant $Dab^9$ derivatives comprise a mixture of compounds which differ from one another with respect to the structures of their macrocyclic peptide cores. Structurally pure $Dab^9$ derivatives may be obtained from this mixture, if desired, by separating and isolating the component $Dab^9$ derivatives using conventional techniques.

In another embodiment, $Dab^9$ derivatives obtained by derivatizing a parent antibiotic as previously described may be delipidated, typically before removing any present protecting groups, and relipidated with a fatty acid moiety having a specified structure. Removal of any present protecting groups yields a $Dab^9$ derivative of the invention. Whether this resultant $Dab^9$ derivative is structurally pure or comprises a mixture of compounds will depend upon whether the $Dab^9$ preparation used as a starting material for the delipidation is structurally pure with respect to the macrocyclic peptide core.

The above-described synthetic pathways yield novel protected intermediates. These intermediates constitute another aspect of the instant invention.

In still another aspect, the present invention provides methods of inhibiting the growth of microbes, such as Gram-positive bacteria. The method generally involves contacting a microbe with one or more compounds of the invention (or an acceptable salt thereof) in an amount effective to inhibit the growth of the microbe. The method may be practiced to achieve a microbistatic effect where the growth of the microbe is inhibited, or to achieve a microbicidal effect, where the microbe is killed.

In a final aspect, the present invention provides methods for treating and/or preventing microbial infections, such as infections caused by Gram-positive bacteria, in a subject such as human, plant or animal. The methods generally involve administering to a subject one or more compounds or compositions of the invention in an amount effective to treat or prevent the infection. The compounds or compositions may be administered systemically or applied topically, depending on the nature of the infection.

5. DETAILED DESCRIPTION OF THE PREFERRED EMBODIMENTS 5.1 Abbreviations

The abbreviations used for the genetically encoded amino acids and certain common non-encoded amino acids are conventional and are as follows:

| Amino Acid | "Three-Letter" | One-Letter |
| --- | --- | --- |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| β-methylaspartate | MeAsp | |
| 2,3-diaminobutyric acid | Dab | |
| Pipecolic acid (homoproline) | Pip or hPro | |
| Sarcosine (N-methyl glycine) | Sar or MeGly | |

Unless specifically specified, amino acids may be in either the D- or L-configuration.

"ATCC" refers to the American Type Culture Collection, Manassas, VA. 20108 (see also http://www.atcc.org).

"NRRL" refers to the Agriculture Research Service Culture Collection, Microbial Genomics and Bioprocessing Research Unit, National Center for Agriculture Utilization Research, Peoria, Ill. 61604 (see also http://nrrl.ncaur.usda.gov).

5.2 Definitions

As used herein, the following terms are intended to have the following meanings:

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl , prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl , but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 4 carbon atoms.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_1$-$C_4$) alkyldiyl. Also preferred are saturated acyclic alkanyldiyl groups in which the radical centers are at the terminal carbons, e.g., methandiyl (methano); ethan-1,2-diyl(ethano); propan-1,3-diyl(propano); butan-1,4-diyl(butano); and the like (also referred to as alkylenos, defined infra).

"Alkyleno" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is ($C_1$-$C_6$) or ($C_1$-$C_4$) alkyleno. Also preferred are straight-chain saturated alkano groups, e.g., methano, ethano, propano, butano, and the like.

"Heteroalkyl, Heteroalkanyl, Heteroalkenyl, Heteroalkanyl, Heteroalkyldiyl and Heteroalkyleno" refer to alkyl, alkanyl, alkenyl, alkynyl, alkyldiyl and alkyleno groups, respectively, in which one or more of the carbon atoms (and any associated hydrogen atoms) are each independently replaced with the same or different heteroatoms or heteroatomic groups. Typical heteroatoms or heteroatomic groups which can be included in these groups include, but are not limited to, —O—, —S—, —Se—, —O—O—, —S—S—, —O—S—, —O—S—O—, —O—NR'—, —NR'—, —NR'—NR'—, =N—N=, —N=N—, —N=N—NR'—, —PH—, —P(O)$_2$—, —O—P(O)$_2$—, —SH$_2$—, —S(O)$_2$—, —SnH$_2$— and the like, and combinations thereof, including, for example, —NR'—S(O)$_2$—, where each R' is independently selected from the group consisting of hydrogen, alkyl, alkanyl, alkenyl, alkynyl, aryl, arylalkyl, heteroaryl and heteroarylalkyl, as defined herein.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$-$C_{14}$) aryl, with ($C_5$-$C_{10}$) being even more preferred. Particularly preferred aryls are cyclopentadienyl, phenyl and naphthyl.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$-$C_{20}$) arylalkyl, e.g., the alkanyl, alkenyl or alkynyl moiety of the arylalkyl group is ($C_1$-$C_6$) and the aryl moiety is ($C_5$-$C_{14}$). In particularly preferred embodiments the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-14 membered heteroaryl, with 5-10 membered heteroaryl being particularly preferred. The most preferred heteroaryl groups are those derived from thiophene, pyrrole, benzothiophene, benzofuran, indole, pyridine, quinoline, imidazole, oxazole and pyrazine.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heterorylalkynyl is used. In preferred embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Amphomycin-Type Lipopeptide Antibiotic" refers to an antibiotic characterized by a macrocyclic peptide core which includes a macrocyclic amino acid having a side chain with a primary amino group, such as a macrocyclic Dab residue, and a lipophilic fatty acid moiety. The macrocyclic peptide core includes an exocyclic amino acid, which is typically an Asn or an Asp, which intervenes the macrocycle and the fatty acid moiety. In one illustrative embodiment, an amphomycin-type lipopeptide antibiotic is characterized by the following structure (I):

(I)

wherein:

$R^1$ is a branched or straight-chained, saturated or singly or multiply unsaturated aliphatic or hydroxy aliphatic moiety having a chain length of from 6 to 22 carbon atoms; and $R^2$ is OH or $NH_2$.

For convenience, amphomycin-type lipopeptide antibiotics may be abbreviated using three different conventions, illustrated below:

(Ia)

$R^3$-$R^4$-$Dab^2$-$Pip^3$-$MeAsp^4$-$Asp^5$-$Gly^6$-$Asp^7$-$Gly^8$-$Dab^9$-$Val^{10}$-$Pro^{11}$

(Ib)

$R^3$-$R^4$-cyclo($Dab^2$-$Pip^3$-$MeAsp^4$-$Asp^5$-$Gly^6$-$Asp^7$-$Gly^8$-$Dab^9$-$Val^{10}$-$Pro^{11}$)

(Ic)

In structures (Ia) and (Ib), $R^3$ is a branched or straight-chained, saturated or singly or multiply unsaturated fatty acid or hydroxy fatty acid having a chain length of from 6 to 22 carbon atoms and $R^4$ is an Asp or Asn residue in which the C-terminal carboxyl group is linked to the α-amino group of residue $Dab^2$ and the N-terminal amino group is linked to the carboxyl group of fatty acid $R^3$. In structure (Ia), the "⎯" designates the linkage of the C-terminal carboxyl group of residue $Pro^{11}$ to the β-amino group of residue $Dab^2$. In structure (Ic), $R^1$ and $R^2$ are as previously defined for structure (I) and R represents the peptide macrocyclic illustrated below:

In the above macrocyclic peptide moiety, the dashed line emanating from residue Dab² indicates the point of attachment to the amide nitrogen of structure (Ic) and the dashed line emanating from residue Dab⁹ indicates the point of attachment to the primary amino group of structure (Ic).

Skilled artisans will recognize that amphomycin-type lipopeptide antibiotics isolated from cultures typically comprise mixtures of compounds that differ with respect to the structures of their amphomycin-type macrocyclic cores (defined below) and/or their fatty acid moieties. The various different compounds comprising the mixture may be separated from one another and isolated either as sub-mixtures or as structurally pure compounds. As used herein, "amphomycin-type lipopeptide antibiotic" is intended to include the mixtures naturally produced by the producing strain, as well as any sub-mixtures and/or structurally pure compounds isolated therefrom.

Common amphomycin-type lipopeptide antibiotics include amphomycin (glumamycin) (Heinemann et al., 1953, *Antibiot. Chemother.* 3:1239-1242; Fujino et al., 1965, *Bull. Chem. Soc. Jap.* 38:515; Bodanszky et al., 1973, *J. Am. Chem. Soc.* 95:2352; Shibata et al., U.S. Pat. No. 3,160,561); aspartocin (Shay et al., U.S. Pat. No. 3,057,779; Shay et al., 1960, *Antibiotics Ann.* 194; Hausman et al., 1964, *Antimicrob. Ag Chemother.* 352; Hausman et al., 1969, *J. Antibiotics* 22:207; Martin et al., 1960, *J. Am. Chem. Soc.* 2079); crystallomycin (Gauze et al., 1957, *Antibiotiki* 2:9-14); antibiotic A1437 (Hammann et al., EP 0 629 636 B1; Hammann et al., U.S. Pat. No. 6,194,383; Lattrell et al., U.S. Pat. No. 5,629,288); friulimycin (Vertesy et al., 2000, *J. Antibiotics* 53:816); tsushimycin (Shoji et al., 1968, *J. Antibiotics* 21:439; Nishimura et al., U.S. Pat. No. 3,781,420); and zaomycin (Hinuma, 1954, *J. Antibiotics* 7(4):134-136; Kuroya, 1960, *Antibiotics Ann.* 194; Kuroya, JP 8150).

"Amphomycin-Type Macrocyclic Core" refers to the macrocycle obtained by delipidating an amphomycin-type lipopeptide antibiotic, illustrated as structural formula (II), below:

(II)

In structure (II), R² is as previously defined for structure (I).

For convenience, amphomycin-type macrocyclic cores may be conveniently abbreviated using three different conventions, illustrated below:

(IIa)

(IIb)

(IIc)

In structures (IIa) and (IIb), $H_2N-R^5$ is an Asp or Asn residue in which the C-terminal carboxyl is linked to the α-amino of residue $Dab^2$. In abbreviation (IIa), the "⌐" designates the linkage of the C-terminal carboxyl of residue $Pro^{11}$ to the β-amino of residue $Dab^2$. In structure (IIc), $R^2$ and R are as previously defined for structure (Ic).

"Structurally Pure" refers to a compound composition in which a substantial percentage, e.g., the order of 95%, 96%, 97%, 98%, 99% or more, of the individual molecules comprising the composition each contain the same number and types of atoms attached to each other in the same order and with the same bonds. As used herein, "structurally pure" is not intended to distinguish different geometric isomers or different optical isomers from one another. For example, as used herein a mixture of cis- and trans-but-2,3-ene is considered structurally pure, as is a racemic mixture. When compositions are intended to include a substantial percentage of a single geometric isomer and/or optical isomer are intended, the nomenclature "geometrically pure" and "optically or enantiomerically pure," respectively, are used.

Nor is the expression "structurally pure" intended to discriminate between different tautomeric forms or ionization states of a molecule, or other forms of a molecule that result as a consequence of equilibrium phenomena or other reversible interconversions. Thus, a composition of, for example, an organic acid is structurally pure even though some of the carboxyl groups may be in a protonated state (—COOH) and others may be in a deprotonated state (—COO—). Likewise, a composition comprising a mixture of keto and enol tantomers, unless specifically noted otherwise, is considered structurally pure.

5.3 The $Dab^9$ Derivatives

The compounds of the invention are derivatives of amphomycin-type lipopeptide antibiotics that are substituted at the β-amino group of the macrocyclic $Dab^9$ residue with a substituent that includes a primary or secondary amine. In one illustrative embodiment, the compounds of the invention are amphomycin-type lipopeptide antibiotic derivatives according to structural formula (III):

including the salts thereof, wherein:

$R^1$ and $R^2$ are as previously defined for structure (I); and $R^6$ is a substituent including a primary or secondary amine.

For convenience of discussion, the compounds of structure (III) may be abbreviated as illustrated in structures (IIIa-c), below:

In structures (IIIa) and (IIIb), $R^3$ and $R^4$ are as previously defined for structure (Ia) and $R^6$ is as defined for structure (III). In structure (IIIc), $R^1$ and $R^2$ are as previously defined for structure (I) and $R^6$ is as previously defined for structure (III). In structures (IIIa) and (IIIb), the $R^6$ substituent is linked to the β-amino group of the illustrated $Dab^9$ residue (see, e.g., structure III).

In some embodiments, the compounds of the invention are $Dab^9$ derivatives of parent amphomycin-type lipopeptide antibiotics produced from cultures. Examples of such parent amphomycin-type lipopeptide antibiotics include, but are not limited to, amphomycin (glumamycin), aspartocin, crystallomycin, friulimycin, tsushimycin and zaomycin. Skilled artisans will recognize that in these embodiments, the structures of residue $R^4$ and/or fatty acid moiety $R^3$ in formulae (Ia) and (Ib) will be dictated in large part by the producing strain and culture conditions. Skilled artisans will also recognize that in these embodiments, the parent amphomycin-type lipopeptide antibiotics may comprise mixtures of compounds that differ from one another with respect to the structure of residue $R^4$ and/or fatty acid moiety $R^3$. As will be discussed in more detail below in connection with the synthesis of the compounds of the invention, the desired compounds of the invention may be obtained by appropriate selection of the parent amphomycin-type lipopeptide antibiotic used as a starting material. For example, although preparations of aspartocin, amphomycin, zaomycin and tsushimycin isolated from cultures comprise mixtures of compounds, they are all believed to share the same amphomycin-type macrocyclic core: the amphomycin-type macrocyclic core of structural formula (II) in which $R^2$ is OH. Likewise, in preparations of friulimycin, the components of the mixture are all believed to share the same amphomycin-type macrocyclic core: the amphomycin-type macrocyclic core of structural formula (II) in which $R^2$ is $NH_2$. Thus, it is believed that the compounds comprising these respective antibiotic mixtures differ from one another only with respect to the structures of their fatty acid moieties. Alternatively, antibiotic A1437 comprises a mixture of compounds that are believed to differ from one another with respect to the structures of their amphomycin-type macrocyclic cores and fatty acid moieties (see, e.g., U.S. Pat. No. 6,194,383).

All of these various parent amphomycin-type lipopeptide antibiotics may be used as starting materials to produce the desired Dab⁹ derivatives of the invention. Structurally pure Dab⁹ derivatives of the invention may be obtained by separating and isolating the component compounds of the parent amphomycin-type lipopeptide antibiotic starting material prior to derivatization of the macrocyclic Dab⁹ residue, or, alternatively, separating the component compounds of the resultant mixture following derivatization, as will be described in more detail, below.

Moreover, in many instances, the exact structures of the fatty acid moieties of such parent amphomycin-type lipopeptide antibiotics are unknown. Compounds of the invention having a fatty acid moiety of a specified structure may be obtained by delipidating the parent amphomycin-type lipopeptide antibiotic starting materials and reacting the delipidated intermediate with a fatty acid of specified structure. The resultant product may then be derivatized at the Dab⁹ residue to yield a Dab⁹ derivative of the invention. Alternatively, a Dab⁹ derivative of the invention prepared by derivatizing a parent amphomycin-type lipopeptide antibiotic may be delipidated and the Dab⁹ derivatized delipidated intermediate reacted with a fatty acid of specified structure. Fatty acids suitable for use in producing an appropriate fatty acid moiety $R^3$ are well-known to skilled artisans (see, e.g., Römpp Chemie Lexicon, Prof. Falbe and Prof. Regitz, 9$^{th}$ Edition, Georg Thieme Verlag Stuttgart, New York; and Hawley, 3$^{rd}$ Edition, Van Nostrand Reinhold Company, New York, each of which is incorporated herein by reference).

In one embodiment, a fatty acid is selected that yields a compound of the invention having a fatty acid moiety $R^3$ that is identical to a fatty acid moiety of a known amphomycin-type lipopeptide antibiotic. Such fatty acids are well-known to those of skill in the art. Non-limiting illustrative examples are provided in, e.g., U.S. Pat. No. 6,194,383 (see especially Cols. 5-8), which is incorporated herein by reference.

However, the fatty acid need not correspond to a fatty acid of a known amphomycin-type lipopeptide antibiotic. Suitable fatty acids include, by way of example and not limitation, the various fatty acids described in U.S. Pat. No. 6,194,383 (see especially Col. 9, in particular at lines 17-53), which is incorporated herein by reference.

Typically, the fatty acid is a fatty acid or hydroxy fatty acid with a chain length of from 6-22 carbon atoms and usually from 10-20 carbon atoms. The fatty acid or hydroxy fatty acid may be branched or linear, saturated or singly or multiply unsaturated, or combinations thereof. In one embodiment, the fatty acid is a saturated or singly unsaturated fatty acid comprising 11, 12, 13, 14 or 15 carbon atoms that is either linear or singly branched, preferably in the iso or ante-iso configuration. In another embodiment, the fatty acid is a saturated or singly unsaturated hydroxy fatty acid comprising 11, 12, 13, 14 or 15 carbon atoms that is either linear or singly branched, preferably in the iso or ante-iso configuration. In a specific embodiment, the hydroxy fatty acid is hydroxylated at position 2, 3 and/or at the end of the chain.

In the compounds of structures (IIIa) and (IIIb), $R^4$ represents an Asp residue or an Asn residue. Whether $R^4$ is Asp or Asn will depend upon the choice of parent amphomycin-type lipopeptide antibiotic used as a starting material in the synthesis of the Dab⁹ derivatives of the invention, as will be apparent to those of skill in the art. For example, Dab⁹ derivatives in which $R^4$ is Asp may be prepared from amphomycin, aspartocin, tsushimycin, and/or the Asp fraction of antibiotic A1437. Dab⁹ derivatives of the invention in which $R^4$ is Asn may be prepared from friulimycin and/or from the Asn fraction of antibiotic A1437. The Asp and Asn fractions of antibiotic A1437 may be isolated from a preparation of cultured antibiotic A1437 according to the methods described in U.S. Pat. No. 6,194,383, which are incorporated herein by reference. Dab⁹ derivatives of the invention which comprise a mixture of compounds, some of which are compounds according to structural formulae (IIIa) or (IIIb) in which $R^4$ is Asp and others of which are compounds according to structural formulae (IIIa) or (IIIb) in which $R^4$ is Asn, may be prepared from antibiotic A1437.

In the Dab⁹ derivatives of structural formulae (III), (IIIa), (IIIb) and (IIIc), $R^6$ represents a substituent that includes a primary or secondary amine group. In one embodiment, the primary or secondary amine group has the formula —$NHR^7$, where $R^7$ is hydrogen or ($C_1$-$C_4$) alkyl. The primary or secondary amine group is typically spaced away from the macrocyclic Dab⁹ residue via a linking moiety which will be described in more detail, below. The present inventor has discovered that amphomycin-type lipopeptide antibiotics derivatized at the macrocyclic Dab⁹ residue with such an $R^6$ substituent retain the antimicrobial properties of the parent amphomycin-type lipopeptide antibiotics from which they are derived, but have different solubility properties, which may lead to the Dab⁹ derivatives having improved therapeutic properties or spectra as compared to the parent amphomycin-type lipopeptide antibiotics from which they are derived.

Figure 1:
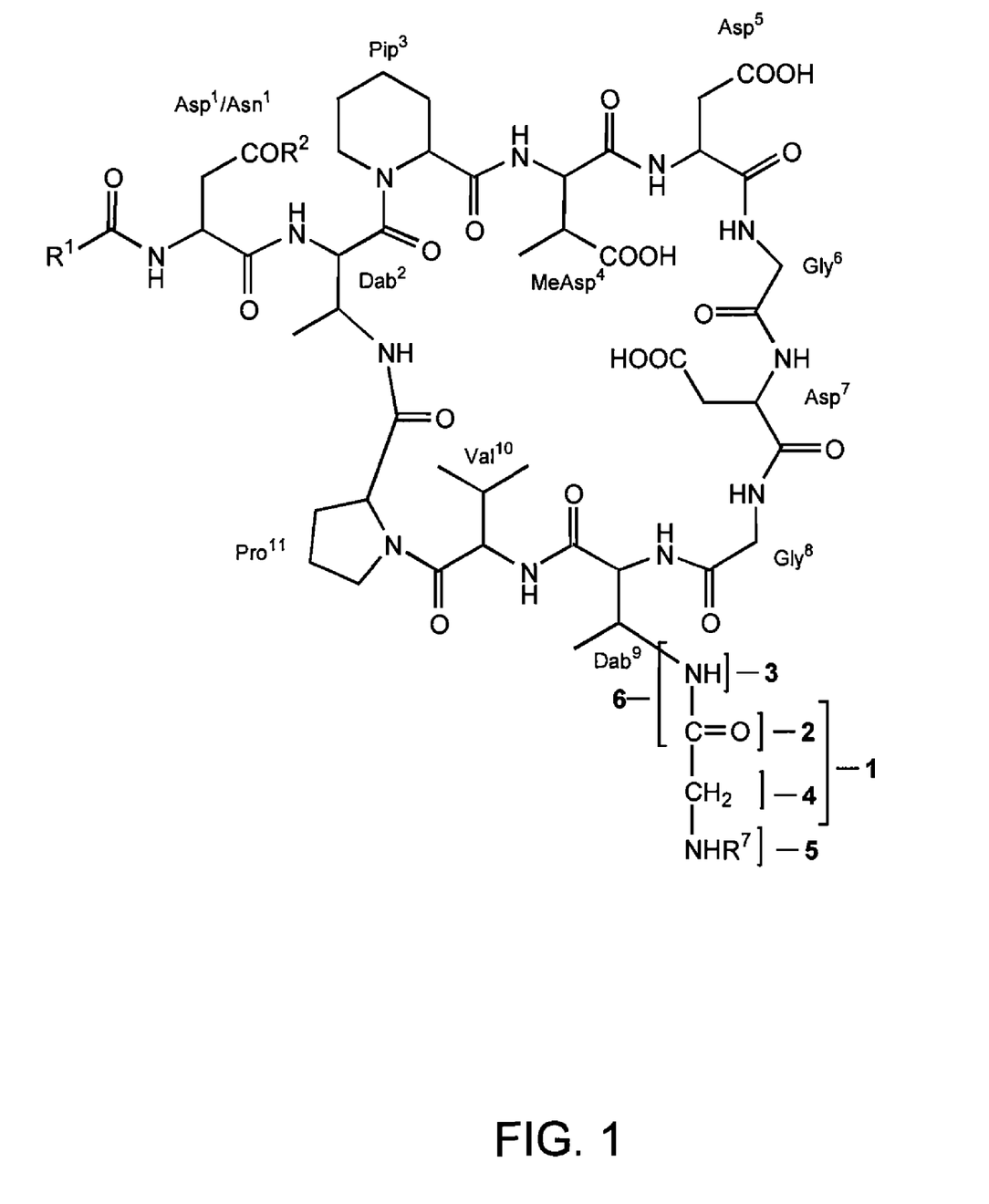
FIG. 1 provides an illustration of a $Dab^9$ derivative of the invention.

As mentioned above, the primary or secondary amine —$NHR^7$ is spaced away from the β-nitrogen of the Dab⁹ residue ("Dab⁹ β-nitrogen") via a linking moiety. Referring to FIG. 1, which illustrates a representative Dab⁹ derivative of the invention in which $R^1$ and $R^2$ are as defined for structural formula (III) and $R^7$ is as defined above, the linking moiety 1 comprises a linkage group 2, which is attached to the Dab⁹ β-nitrogen 3, and an optional spacer 4. Taken together, the linkage group 2 and spacer 4 comprise a sufficient number of atoms such that the distance between the Dab⁹ β-nitrogen 3 and the nitrogen atom of the amine group —$NHR^7$ ("amine nitrogen") 5 is in the range of about 1-10 Å. Typically, the linkage group 2 is a moiety that, when taken together with the Dab⁹ β-nitrogen atom 3 to which it is bonded, yields a linkage 6 that is stable to the physiologic conditions under which the compounds of the invention will be used. Non-limiting examples of suitable linkages 6 include amide, sulfonamide, amidine, carbonate and urea linkages. Accordingly, non-limiting examples of suitable linking groups 2 include —C(O)—, —S(O)$_2$—, —C(NH)— and —C(O)O— groups.

The spacer 4, which may be present or absent, may include virtually any combination of carbon and/or heteroatoms suitable for spacing the primary or secondary amine group away from the linkage formed between the linking group and the Dab⁹ β-nitrogen. Suitable groups which may comprise the spacer 4 include, but are not limited to —CH$_2$—, —CH=CH—, —C≡C—, —O—, —S—, —NH—, —NH—NH—, —N=N—, —C(O)—, —S(O)$_2$—, —S(O)$_2$—O— and —C(NH)— groups. These and other groups that will be apparent to those of skill in the art may be used in a multitude of combinations to create suitable spacers 4. Skilled artisans will recognize that the exact number of atoms necessary to achieve the appropriate spacing will depend upon, among other things, the types of atoms (e.g., N, O, C, etc.) and bonds (e.g., single, double, triple, etc.) comprising the linking moiety 1 and will be able to select combinations of groups yielding an appropriate spacing.

One or more of the atoms comprising the spacer 4 may be substituted with a substituent. The substituent may be virtually any group that can be attached to the type of atom being substituted. In one embodiment, such substituents, which may be the same or different, are selected from the group consisting of —$NR^8R^8$, —$OR^8$, —$SR^8$, halogen, trihalomethyl, —CN, —C(O)$R^8$, —C(O)O$R^8$, —C(O)N$R^8R^8$, amidine, guanidine, alkyl, alkyl substituted with one or more of the same or different $R^9$, aryl, aryl substituted with one or more of the same or different $R^9$, arylalkyl, arylalkyl substituted with one or more of the same or different $R^9$, heteroalkyl, heteroalkyl substituted with one or more of the same or different $R^9$, heteroarylalkyl and heteroarylalkyl substituted with one or more of the same or different $R^9$, where each $R^8$ is independently selected from the group consisting of hydrogen, alkyl, aryl, arylalkyl, heteroaryl and heteroarylalkyl, and each $R^9$ is independently selected from the group consisting of —$NR^8R^8$, —$OR^8$, —$SR^8$, halogen, trihalomethyl, —CN, —$C(O)R^8$, —$C(O)OR^8$, —$C(O)NR^8R^8$, amidine, guanidine, alkyl, aryl, arylalkyl, heteroaryl and heteroarylalkyl.

In one embodiment of the invention, the spacer 4 is a ($C_1$-$C_6$) branched or unbranched alkyldiyl which optionally includes one or more, typically one, of the same or different previously described substituent groups. Preferred alkyldiyls are substituted or unsubstituted alkylenos. Especially preferred alkyldiyls are substituted or unsubstituted ($C_1$-$C_4$) alkenos.

Thus, in one illustrative embodiment of the $Dab^9$ derivatives according to structural formulae (III), (IIIa), (IIIb) and (IIIc), amine-containing substituent $R^6$ has the structural formula (IV):

wherein:
$R^7$ is as previously defined;
$R^{10}$ is ($C_1$-$C_4$) alkano; and
X is —C(O)—, —C(NH)— or —$S(O)_2$—.

In another illustrative embodiment of the $Dab^9$ derivatives of structural formulae (III), (IIIa), (IIIb) and (IIIc), amine-containing substituent $R^6$ has the structural formula (V):

wherein:
n is an integer from 1 to 6;
each $R^{11}$ is independently selected from the group consisting of hydrogen, amino, amido, amidino, carboxy, guanidino, hydroxy, sulfanyl, ($C_1$-$C_4$) alkyl, ($C_1$-$C_4$) alkyl substituted with one or more of the same or different $R^{12}$, ($C_5$-$C_{10}$) aryl, ($C_5$-$C_{10}$) aryl substituted with one or more of the same or different $R^{12}$, ($C_6$-$C_{13}$) arylalkyl, ($C_6$-$C_{13}$) arylalkyl substituted with one or more of the same or different $R^{12}$, 5-10 membered heteroaryl, 5-10 membered heteroaryl substituted with one or more of the same or different $R^{12}$, 6-13 membered heteroarylalkyl and 6-13 membered heteroarylalkyl substituted with one or more of the same or different $R^{12}$;

each $R^{12}$ is independently selected from the group consisting of amino, amido, amidino, carboxyl, guanidino, hydroxy and sulfanyl; and

X and $R^7$ are as previously defined for structure (IV).

In a specific embodiment of structural formula (V), n is 1, 2 or 3 and/or only one $R^{11}$ is other than hydrogen.

In another illustrative embodiment of the $Dab^9$ derivatives of structural formulae (III), (IIIa), (IIIb) and (IIIc), substituent $R^6$ is an amino acid which is linked via its terminal carboxyl group to the β-amino group of the macrocyclic $Dab^9$ residue to form an amide linkage. Such amino acids may include, by way of example and not limitation, α-, β- and γ-amino acids. The amino acids may optionally include side chain moieties, such as a side chain moiety of one of the twenty genetically encoded amino acids, or a common analog thereof. Any chiral centers in the amino acid may be in either the R- or S-configuration. Non-limiting examples of suitable amino acids include the twenty genetically encoded amino acids; the various amino acids listed in Fasman, *CRC Practical Handbook at Biochemistry and Molecular Biology*, 1989, CRC Press, Inc., Boca Raton, Fla. at pp. 4-60, the disclosure of which is incorporated herein by reference, and the α, β-unsaturated amino acids listed in Fasman, 1989, supra, at pp. 69, the disclosure of which is incorporated herein by reference. Other suitable amino acids will be apparent to those of skill in the art.

5.4 Methods of Synthesis

The compounds of the invention may be synthesized via several different synthetic routes using commercially available starting materials and/or starting materials prepared by conventional synthetic and/or biosynthetic methods. Two general synthetic approaches are illustrated in Scheme (I), below:

In Scheme (I), $R^1$ and $R^2$ are as previously defined in structural formula (IIIc). According to Scheme (I), a parent amphomycin-type lipopeptide antibiotic 10 is acylated with an appropriately protected reactant 12, which in the specific illustrated example is Fmoc-protected glycine, to yield protected intermediate 14. Reaction conditions for coupling primary amines such as antibiotic 10 with carboxylic acids such as reactant 12 to yield amide linkages are known to those of skill in the art and may be found in any compendium of standard synthetic methods and/or literature related to the synthesis of peptides and proteins. See e.g., March, J., *Advanced Organic Chemistry; Reactions, Mechanisms and Structure*, 4$^{th}$ ed., 1992; Larock, *Comprehensive Organic Transformations*, VCH, New York, 1999; Bodanzsky, *Principles of Peptide Synthesis*, Springer Verlag, 1984; Bodanzsky, *Practice of Peptide Synthesis*, Springer Verlag, 1984; Lloyd-Williams et al., *Chemical Approaches to the Synthesis of Peptides and Proteins*, CRC Press, 1997 (see especially pp. 105-114); and Atherton & Sheppard, *Solid Phase Peptide Synthesis: A Practical Approach*, IRL Press, 1989, each of which is incorporated herein by reference). Specific conditions are provided in the Examples section, infra.

Protected intermediate 14 is then deprotected to yield Dab$^9$ derivative 16. While the method is illustrated using an Fmoc protecting group, skilled artisans will recognize that other protecting groups may be employed. Moreover, in some instances, reactant 12 may include other and/or additional functionalities that may require protection. Groups suitable for protecting a wide variety of different functionalities, as well as conditions for their removal, are well-known and will be apparent to those of skill in the art. Specific guidance for selectively protecting a wide variety of functionalities may be found, for example, in Greene & Wuts, *Protective Groups in Organic Synthesis*, 3$^{rd}$ edition, 1999 ("Greene & Wuts"), which is incorporated herein by reference. Preferred protecting groups are those that may be easily removed. Preferred groups for protecting primary amines are tert-butyloxycarbonyl ("t-Boc"), 9-fluorenylmethoxycarbonyl ("Fmoc") and benzyloxycarbonyl ("Z").

Parent amphomycin-type lipopeptide antibiotic 10 may be obtained by isolation from a culture of a microorganism known to produce the antibiotic. Microorganisms for producing amphomycin-type lipopeptide antibiotics are well-known, as are conditions for isolating, and optionally further purifying, the resultant antibiotics. For example, strains for producing amphomycin (glumamycin) include *Streptomyces canus* (ATCC #12237; see also Heinemann et al., 1953, *Antibiot. Chemother.* 3:1239-1242) and *Streptomyces zaomyceticus* (ATCC #13876; see also U.S. Pat. No. 3,160,561 to Shibata et al.). Strains for producing aspartocin include *Streptomyces griseus* subspecies *sprialis* (ATCC #13733; see also U.S. Pat. No. 3,057,779 to Shay et al.) and *Streptomyces violaceus* (Rossi-Doria) Waksman (ATCC #13734; see also U.S. Pat. No. 3,057,779). Strains for producing crystallomycin include *Streptomyces violaceoniger* var. *crystallomycini* (Gauze et al., 1957, Antibiotiki 2(6):9-14). Strains for producing antibiotic A1437 include *Actinoplanes* sp. (DSM #7358; see also U.S. Pat. No. 6,194,383 to Hammann et al.) Strains for producing friulimycin include *Actinoplanes friuliensis* (HAG #010964). Strains for producing tsushimycin include *Streptomyces pseudogriseolus* Okami and Umezawa (ATCC pseudogriseolus #21139 and #21140; see also U.S. Pat. No. 3,781,420 to Nishimura et al.) and *Streptomyces pseudogriseolus* subspecies *glucofermentans* Nishimura and Otsuka (ATCC #21141; see also U.S. Pat. No. 3,781,420 to Nishimura et al.). Strains for producing zaomycin include *Streptomyces zaomyceticus* Hinuma (NRRL #B-2038). Conditions for culturing and isolating the various lipopeptide antibiotics are found in the above-cited patents and references, as well as the various references mentioned previously in connection with these various antibiotics, the disclosures of which are incorporated herein by reference.

As discussed previously, in most instances, amphomycin-type lipopeptide antibiotics 10 isolated from cultures are mixtures of compounds that differ with respect to the structures of $R^1$ and/or $R^2$. For example, amphomycin is a mixture of compounds 10 in which $R^2$ is OH and the fatty acid moiety $R^1$—C(O)— is a mixture of iso and ante-iso $C_{12}$ and $C_{13}$ fatty acids. Aspartocin is a mixture of compounds 10 in which $R^2$ is OH and the fatty acid moiety $R^1$—C(O)— is a mixture of iso and ante-iso $C_{13}$ and $C_{14}$ fatty acids. Tsushimycin is a mixture of compounds 10 in which $R^2$ is OH and the fatty acid moiety $R^1$—C(O)— is a mixture of iso and ante-iso $C_{14}$ and $C_{15}$ fatty acids. Friulimycin is a mixture of compounds 10 in which $R^2$ is $NH_2$ and the fatty acid moiety $R^1$—C(O)— is a mixture of iso and ante-iso $C_{13}$ and $C_{15}$ fatty acids. Antibiotic A1437 is a complex mixture of 11 compounds, some of which $R^2$ is OH and in others of which $R^2$ is $NH_2$ and the fatty acid moiety is a mixture of iso and ante-iso $C_{13}$, $C_{14}$ and $C_{15}$ fatty acids. In many instances, culture conditions useful for producing one or more of the compounds of the mixtures in greater or lesser yields are known (see, e.g., J. Biotechnology 7:283-292, 1988). Such methods may be used in conjunction with the invention to provide mixtures of $Dab^9$ derivatives having fatty acid moieties of defined molar ratios.

Amphomycin-type lipopeptide antibiotics 10 isolated from cultures may be used directly in Scheme (I) without prior separation and isolation of the various components of the mixtures, or they may be first separated, either with respect to the fatty acids and/or, in the case of antibiotic A1437, with respect to $R^2$, into structurally pure compounds or sub-fractions or sub-mixtures. Methods for separating individual components or sub-mixtures of antibiotic preparations are well-known and will be apparent to those of skill in the art. Specific suitable methods are provided, for example, in U.S. Pat. No. 6,194,383 (see especially Cols. 10-12), which is incorporated herein by reference, and in the Examples section, infra.

In many instances, the structures of the fatty acid moieties of amphomycin-type lipopeptide antibiotics 10 may be unknown. In instances where $Dab^9$ derivatives of the invention having specified fatty acid moieties are desired, or where it is desirable for the $Dab^9$ derivative to be structurally pure, geometrically pure or optically pure, with respect to the fatty acid moiety, rather than isolating components of a cultured antibiotic preparation, it may be more convenient or desirable to replace the natural fatty acid moiety of the cultured antibiotic 10 with a synthetic fatty acid moiety of specified structure. As illustrated in Scheme (I), this may be achieved by several synthetic strategies.

According to a first strategy, amphomycin-type lipopeptide antibiotic 10 is first protected at the β-amino group of the macrocyclic $Dab^9$ residue to yield protected intermediate 18. Again, while the illustrated protecting group is Fmoc, skilled artisans will appreciate that other commonly-known amine protecting groups may be used. Protected intermediate 18 is then delipidated to yield protected amphomycin-type macrocyclic core 20. Protected core 20 is then acylated with fatty acid 22, again using standard chemistries, to yield protected amphomycin-type lipopeptide antibiotic 24. In fatty acid 22, $R^{11}$ represents the aliphatic chain of the fatty acid, and may be any of the aliphatic or hydroxy aliphatic chains previously described for $R^1$ of structure (III).

Protected antibiotic 24 is the deprotected to yield compound 26, reacted with reagent 12 to yield protected $Dab^9$ derivative 28 which, following deprotection, yields $Dab^9$ derivative 30. When parent amphomycin-type lipopeptide antibiotic 10 is a mixture of compounds that all share the same amphomycin-type macrocyclic core, such as amphomycin, aspartocin, friulimycin, tsushimycin or zaomycin, this method may be used to synthesize $Dab^9$ derivatives of the invention that are structurally pure without having to isolate the various fatty acid fractions of the parent amphomycin-type lipopeptide antibiotic 10 from one another. Delipidation yields a mixture comprising the various fatty acids and the protected amphomycin-type macrocyclic core. The protected macrocyclic core may be readily isolated in high purity from this mixture using any art-known technique, such as high performance liquid chromatography, counter current extraction, centrifugation, filtration, precipitation, ion exchange chromatography, gel electrophoresis, affinity chromatography, etc. Specific procedures that may be used directly or that may be routinely adapted to isolate a particular protected macrocyclic core are described in Debono et. al., 1988, J. Antibiotics 41:1093 and U.S. Pat. No. 5,039,789 (see, e.g., Cols. 30-34), each of which is incorporated herein by reference. Additional chemistries and procedures that may be used directly to delipidate and relipidate parent amphomycin-type lipopeptide antibiotic 10 are found in U.S. Pat. No. 5,629,288 to Lattrell et al., the disclosure of which is incorporated herein by reference.

In an alternative route, protected $Dab^9$ derivative 14 is delipidated and acylated with fatty acid 22, yielding protected $Dab^9$ derivative 28 which, following deprotection, yields $Dab^9$ derivative 30. This alternative route is advantageous in that it does not require separate protection of the macrocyclic $Dab^9$ β-amino group.

Generally, the fatty acid moiety of protected amphomycin-type lipopeptide antibiotic 18 and/or protected $Dab^9$ derivative 14 may be cleaved with an enzyme. The enzyme may be, for example, a degradative enzyme such as a peptidase, esterase or thiolase, of which numerous examples exist in the art. Preferably, the enzyme is a deacylase.

In an exemplary embodiment, the cleavage step involves culturing a microorganism that produces a deacylase in an appropriate culture medium and contacting protected $Dab^9$ derivative 14 or protected antibiotic 18 with the culture medium containing the deacylase. Microorganisms that produce deacylases are well known to those of skill in the art. In a preferred embodiment, the microorganism *Actinoplanes utahensis* (NRRL #12052) produces a suitable deacylase.

Growing inocula, inoculating media, culturing media and conditions for culturing such enzymes are also well known to those of skill in the art and exemplary methods for *Actinoplanes utahensis* (NRRL #12052) are described in Boeck et al., 1988, J. Antibiot. 41:1085; Debono et. al., 1988, J. Antibiotics 41:1093; U.S. Pat. No. 4,524,135 (see, e.g., Cols. 22-23) and U.S. Pat. No. 5,039,789 (see, e.g., Col. 29, lines 9-63); each of which is incorporated herein by reference.

In one embodiment, compounds 14 or 18 are delipidated by contacting them with a culture medium comprising *Actinoplanes utahensis* (NRRL #12052) for about 4 to 16 hours at a temperature of about 29° C. The reaction may be monitored by chromatography or other routine techniques, thereby permitting shorter or longer incubations, as needed. Additional methods which may be used to delipidate compounds 14 and/or 18 are found in Debono et. al., 1988, J. Antibiotics 41:1093; U.S. Pat. No. 5,039,789 (see, e.g., Cols. 29-34) and U.S. Pat. No. 5,629,288, each of which is incorporated herein by reference.

While Scheme (I) illustrates certain $Dab^9$ derivatives of the invention in which substituent $R^6$ is attached to the macrocyclic $Dab^9$ residue via an amide linkage, those of skill in the art will recognize that $Dab^9$ derivatives including other linkages may be synthesized by routine modification of the illustrated schemes. Moreover, in some instances, substituent $R^6$ may include additional functionalities requiring protection. The identity of the protecting group will depend upon, among other things, the functionality being protected and other protecting groups present on the molecule, and will be apparent to those of skill in the art. Guidance may be found in Greene & Wuts, supra.

The $Dab^9$ derivatives of the invention may be isolated and purified using standard techniques such as high performance liquid chromatography, counter current extraction, centrifugation, filtration, precipitation, ion exchange chromatography, gel electrophoresis, affinity chromatography, etc. Specific methods of isolation are provided in the Examples section, infra. Any of the various parent antibiotics, reaction, intermediates and/or $Dab^9$ derivatives of the invention may also be isolated and purified using the extractive purification methods described in application Ser. No. 60/286,254, filed Apr. 24, 2001, which is incorporated herein by reference.

Those of skill in the art will appreciate that many of the $Dab^9$ derivatives of the invention, as well as the various compound species specifically described herein, may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

Moreover, although the exact optical configurations of the chiral centers of the various illustrated amphomycin-type macrocyclic cores are not specified, it is to be understood that the structural illustrations are intended to be a short-hand way of describing these cores, and are not intended to be limiting. It will be understood that the specific optical configurations are those possessed by the macrocyclic cores of the amphomycin-type lipopeptide antibiotics, whether they are known or unknown.

Also, while these structures of the peptide macrocycles comprising the various parent amphomycin-type lipopeptide antibiotics from which the $Dab^9$ derivatives of the invention are derived are believed to be correct, in some instances later date may reveal errors. Again, the structural illustrations are intended to be a short-hand way of describing the various compounds and are not intended to be limiting. It will be understood that in the $Dab^9$ derivatives of the invention, the structures of the peptide macrocycles are those possessed by the parent amphomycin-type lipopeptide antibiotics from which the specific derivatives are derived.

5.5 Antimicrobial Activity

The $Dab^9$ derivatives of the invention generally exhibit antimicrobial activity against Gram-positive bacteria that is similar to that exhibited by conventional amphomycin-type lipopeptide antibiotics, as measured in in vitro assays. Moreover, many of the $Dab^9$ derivatives of the invention may display improved therapeutic potential, such as reduced toxicity, as compared with conventional amphomycin-type lipopeptide antibiotics, making the $Dab^9$ derivatives of the invention particularly suited for systemic administration to combat infections caused by Gram-positive bacteria.

Generally, active $Dab^9$ derivatives of the invention are identified using conventional in vitro screening assays such as standard NCCLS bacterial inhibition assays, or MIC tests. See, e.g., National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically—Third Edition," Approved Standard M7-A3, National Committee for Clinical Standards, Villanova, Pa. ("Approved Standard M-7-A3"). Compounds considered active will typically exhibit MICs of less than about 64 µg/mL, usually less than about 32 µg/mL, preferably less than about 16 µg/mL and most preferably less than about 4 µg/mL against Gram-positive bacterial such as Strepto-, Staphylo- and Enterococci in these standard assays. Of course, compounds having MICs on the low end of these ranges, or even lower, are preferred. Most preferred for use in treating or preventing systemic infections are $Dab^9$ derivatives that exhibit significant antimicrobial activity (i.e., less than 4 µg/mL) and low toxicity. Systemic toxicity is less of a concern for topical administration. Specific assays suitable for demonstrating antimicrobial activity are provided in the Examples section.

5.6 Uses and Compositions

The antimicrobial $Dab^9$ derivatives of the invention can be used in a wide variety of applications to inhibit the growth of or kill microorganisms. For example, the antimicrobial $Dab^9$ derivatives may be used as disinfectants or as preservatives for materials such as foodstuffs, cosmetics, medicaments and other nutrient containing materials. The antimicrobial $Dab^9$ derivatives can also be used to treat or prevent diseases related to or caused by microbial infection in subjects such as plants and animals, including humans.

For use as a disinfectant or preservative, the antimicrobial $Dab^9$ derivatives can be added to the desired material singly, as mixtures of antimicrobial $Dab^9$ derivatives, or in combination with other antifungal and/or antimicrobial agents. The antimicrobial $Dab^9$ derivatives may be supplied as the compound per se or may be in mixture or admixture with a variety of carriers, diluents or excipients, which are well known in the art.

When used to treat or prevent microbial infections or diseases related thereto, the antimicrobial $Dab^9$ derivatives of the invention can be administered or applied singly, as mixtures of two or more antimicrobial $Dab^9$ derivatives, in combination with other antifungal, antibiotic or antimicrobial agents or in combination with other pharmaceutically active agents. The antimicrobial $Dab^9$ derivatives can be administered or applied per se or as pharmaceutical compositions. The specific pharmaceutical formulation will depend upon the desired mode of administration, and will be apparent to those having skill in the art. Numerous compositions for the topical or systemic administration of antibiotics are described in the literature. Any of these compositions may be formulated with the antimicrobial $Dab^9$ derivatives of the invention.

Pharmaceutical compositions comprising the antimicrobial $Dab^9$ derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active antimicrobial $Dab^9$ derivatives into preparations which can be used pharmaceutically. Proper formulation is dependent upon the route of administration chosen.

For topical administration the antimicrobial $Dab^9$ derivatives of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the antimicrobial $Dab^9$ derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the antimicrobial Dab$^9$ derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the antimicrobial Dab$^9$ derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The antimicrobial Dab$^9$ derivatives may also be formulated in rectal or vaginal compositions such as suppositories or retention enemas, e.g., containing conventional suppository bases such as cocoa butter or other glycerides.

In addition to the formulations described previously, the antimicrobial Dab$^9$ derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the antimicrobial Dab$^9$ derivatives of the invention. Certain organic solvents such as dimethylsulfoxide also may be employed, although usually at the cost of greater toxicity. Additionally, the antimicrobial Dab$^9$ derivatives may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days.

As certain of the carboxyl groups of the antimicrobial Dab$^9$ derivatives of the invention are acidic, and/or the substituent R$^6$ may include acidic or basic substituents, the antimicrobial Dab$^9$ derivatives may be included in any of the above-described formulations as the free acids, the free bases or as pharmaceutically acceptable salts. Pharmaceutically acceptable salts are those salts which retain substantially the antimicrobial activity of the free acids or bases and which are prepared by reaction with bases or acids, respectively. Suitable acids and bases are well-known to those of skill in the art. Pharmaceutical salts tend to be more soluble in aqueous and other protic solvents than are the corresponding free base or acid forms.

The antimicrobial Dab$^9$ derivatives of the invention, or compositions thereof, will generally be used in an amount effective to achieve the intended purpose. Of course, it is to be understood that the amount used will depend on the particular application.

For example, for use as a disinfectant or preservative, an antimicrobially effective amount of an antimicrobial Dab$^9$ derivative, or composition thereof, is applied or added to the material to be disinfected or preserved. By "antimicrobial effective amount" is meant an amount of an antimicrobial Dab$^9$ derivative or composition that inhibits the growth of, or is lethal to, a target microbe. While the actual amount will depend on the particular target microbe and application, for use as a disinfectant or preservative, the antimicrobial Dab$^9$ derivatives, or compositions thereof, are usually added or applied to the material to be disinfected or preserved in relatively low amounts. Typically, the antimicrobial Dab$^9$ derivatives comprise less than about 5% by weight of the disinfectant solution or material to be preserved, preferably less than about 1% by weight and more preferably less than about 0.1% by weight. An ordinarily skilled artisan will be able to determine antimicrobially effective amounts of particular antimicrobial Dab$^9$ derivatives for particular applications without undue experimentation using, for example, the in vitro assays discussed above.

For use to treat or prevent microbial infections, the antimicrobial Dab$^9$ derivatives of the invention, or compositions thereof, are administered or applied in a therapeutically effective amount. By "therapeutically effective amount" is meant an amount effective to ameliorate the symptoms of, or ameliorate, treat or prevent microbial infections. Determination of a therapeutically effective amount is well within the capabilities of those skilled in the art, especially in light of the detailed disclosure provided herein.

As in the case of disinfectants and preservatives, a therapeutically effective dose for topical administration to treat or prevent microbial infections can be determined using, for example, the in vitro assays discussed above. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating antimicrobial Dab$^9$ derivative concentration range that includes the MIC as determined in cell culture.

Initial dosages can also be estimated from in vivo data, e.g., animal models, using techniques that are well known in the art. One having ordinary skill in the art can readily optimize administration to humans based on animal data.

Alternatively, initial dosages can be determined from the dosages administered of known amphomycin-type lipopeptide antibiotics (e.g., amphomycin, aspartocin, crystallomycin, antibiotic A1437, friulimycin, glumamycin, tsushimycin and zaomycin) by comparing the MIC of the specific antimicrobial $Dab^9$ derivative with that of the known antimicrobial agent, and adjusting the initial dosages accordingly. The optimal dosage may be obtained from these initial values by routine optimization.

Dosage amount and interval may be adjusted individually to provide plasma levels of the active antimicrobial $Dab^9$ derivative which are sufficient to maintain therapeutic effect. Usual patient dosages for administration by injection range from about 0.1 to 200 mg/kg/day, but more typically range from about 1.5 to 15 mg/kg/day. Therapeutically effective serum levels may be achieved by administering a single dose daily or multiple doses each day.

In cases of local administration or selective uptake, the effective local concentration of antimicrobial $Dab^9$ derivative may not be related to plasma concentration. One having skill in the art will be able to optimize therapeutically effective local dosages without undue experimentation.

The amount of antimicrobial $Dab^9$ derivative administered will, of course, be dependent on, among other factors, the subject being treated, the subject's weight, the severity of the affliction, the manner of administration and the judgment of the prescribing physician.

The antimicrobial therapy may be repeated intermittently while infections are detectable, or even when they are not detectable. The therapy may be provided alone or in combination with other drugs, such as for example other antibiotics or antimicrobials, or other antimicrobial $Dab^9$ derivatives of the invention.

Preferably, a therapeutically effective dose of the antimicrobial $Dab^9$ derivatives described herein will provide therapeutic benefit without causing substantial toxicity. Toxicity of the antimicrobial $Dab^9$ derivatives can be determined using standard pharmaceutical procedures in cell cultures or experimental animals, e.g, by determining the $LD_{50}$ (the dose lethal to 50% of the population) or the $LD_{100}$ (the dose lethal to 100% of the population). The dose ratio between toxic and therapeutic effect is the therapeutic index. Antimicrobial $Dab^9$ derivatives which exhibit high therapeutic indices are preferred. The data obtained from these cell culture assays and animal studies can be used in formulating a dosage range that is not toxic for use in human subjects. The dosage of the antimicrobial $Dab^9$ derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g. Fingl et al., 1975, *In: The Pharmacological Basis of Therapeutics*, Ch. 1).

The invention having been described, the following examples are intended to illustrate, and not limit, the invention.

6. EXAMPLES

6.1 Compound Synthesis

A number of $Dab^9$ derivatives of aspartocin were prepared according to Scheme (I) from cultured aspartocin, both with and without prior separation and isolation of the various fatty acid fractions. In the nomenclature used herein, "$natC_{14}$" designates the isolated $C_{14}$ fatty acid fraction of the indicated compound and "$natC_{15}$" designates the isolated $C_{15}$ fatty acid fraction of the designated compound. The substituent $R^6$ attached to the β-amino group of the macrocyclic $Dab^9$ residue follows the name of the parent amphomycin-type lipopeptide antibiotic (in parentheses).

6.1.1 Fermentation of Aspartocin in a Bioreactor

The aspartocin complex was produced by fermentation in a 700-liter stainless steel bioreactor. Biochemical synthesis of aspartocin is performed by inoculating a medium composed of 1.0% dextrose, 0.5% molasses, 1.0% Bacto Peptone, and 0.1% $CaCO_3$ in 100 mL of tap water, with spore and mycelial scrapings from a slant of *Streptomyces griseus* ssp. *spiralis* (NRRL B-3290; BSP-M707). The inoculated medium is incubated at a temperature of about 28° C. on a rotary shaker at about 180 rotations per minute (RPM) for about 48 hours providing a substantial and uniform vegetative growth. This seed growth, 10 ml, was transferred to 400 ml of the same medium in a 2-liter flask which was incubated under the same conditions and then added to 9.6 liters of the same medium in a 16-liter fermentor to give the $3^{rd}$ stage seed after 48 hrs., 200 rpm, 5 Lpm air flow. This final seed stage was used to inoculate 500 liters of medium containing 1 g/L $CaCO_3$, 10 g/L Grandma's Molasses (unsulfered), 10 g/L Difco Bacto Peptone, and 20 g/L Baker Dextrose adjusted to pH 7.1 prior to sterilization. Fermentation was conducted with agitation speed 200 rpm, air flow 125 Lpm, and 28° C. with addition of antifoam, Mazu DF204, as required. Fermentation was harvested after 114 hours.

6.1.2 Process to Obtain Crude Preparation

The cells and other solids from the fermentation broth were removed by centrifuge and the supernate, 470 L, was adjusted to pH 3.3 with HCl and allowed to stand at 14° C. for 2 hours. A precipitate was removed by centrifuge and discarded. The decant adjusted to pH 7.0 to which ammonium sulfate was added to cause precipitation of the crude antibiotic complex. The precipitate was separated by centrifuge, dissolved in water, adjusted to pH 7.0, and freeze dried to obtain 2058 g of solid containing 5-7% of the aspartocin complex. Further purification was accomplished by the chelate procedure described below.

6.1.3 Extractive Purification of Aspartocin

A dark colored crude preparation, 68.3 grams, containing 5-7% of the aspartocin complex was dissolved in 500 ml distilled water and stirred as it was adjusted to pH 7.0 to obtain best water solubility. Some insoluble material was separated by centrifuge and the decant was adjusted to pH 3.5. The aspartocin complex was extracted by two sequential 1-butanol extractions (500 ml, 300 ml) and 600 ml of water were added to the combined butanol phases. The resulting two phase system was stirred and adjusted to pH 8.0 with 1 N NaOH to provide the aspartocin complex as the sodium salt in the aqueous phase. Calcium chloride (2.642 g) was added to the separated aqueous phase, and the aspartocin extracted into 1-butanol as a chelate by two sequential extractions (500 ml, 250 ml). To remove calcium, the 1-butanol phases were combined, mixed with 900 ml water, adjusted to pH 3.0, separated from the aqueous phase, and washed with 150 ml of water. The 1-butanol phase containing the aspartocin complex was combined with 500 ml water and adjusted to pH 7.0. To remove some residual pigments, the aqueous phase containing the antibiotic complex was adjusted to pH 3.0 and mixed with 500 ml of 1-butanol. The 1-butanol phase was separated, washed with 150 ml water (pH 2-3), and combined with 500 ml water and the mixture adjusted to pH 7.0. The aqueous phase containing the aspartocin complex as a partial sodium salt was evaporated under vacuum to remove residual 1-butanol and freeze-dried to obtain 3.6 g of a white powder. HPLC analysis of the purified complex showed that the aspartocin complex was approximately 90% pure by 215 nm area % with peaks of the complex between 9.4 to 10.6 minutes. The HPLC system utilized a Prodigy® 5 μODS(2) column eluted with an eight minute gradient of 10% to 75% acetonitrile at pH 7.2 with 0.05 M phosphate buffer.

6.1.4 Synthesis of Aspartocin(Dab$^9$-N-Glycyl)

A solution of N-(9-Fluorenylmethoxycarbonyl) glycine (12.5 mg, 41.7 μmol) and O-benzotriazol-1-yl-N,N,N',N'-tetramethyluronium hexafluorophosphate ("HBTU"; 15.8 mg, 41.7 μmol) in 0.75 mL of DMF was stirred at ambient temperature for 1 hour. Aspartocin (50 mg, 37.9 μmol), prepared as described above, was added to the reaction mixture and stirred for 30 minutes, afterwhich time all of the aspartocin was acylated as detected by ion spray mass spectrometry. Piperidine (0.2 mL) was added in one portion and the solution was stirred for 15 minutes. The reaction mixture was worked up by addition of saturated aqueous solution of ammonium chloride (1 mL) as well as methanol (2 mL). The mixture was filtered and purified by reverse phase HPLC (70:30-10:90 of A:B in which A=90% H$_2$O, 10% acetonitrile ("ACN"), 0.1% trifluoroacetic acid ("TFA") and B=90% ACN, 10% H$_2$O, 0.1% TFA) over 32 minutes with a flow rate of 6.0 mL/min using a C18 Hyperprep BDS column from National Scientific (150×20 mm). The aspartocin(Dab$^9$-N-glycyl) product eluted at approx. 30 minutes, with the C$_{14}$ fraction eluting at about 29 min. and the C$_{15}$ fraction eluting at about 29.5-30 min. Purity of each fraction from prep HPLC was further analyzed by reverse phase HPLC (100% A to 100% B in which A=90% ammonium phosphate buffer at pH=7.1, 10% ACN and B=85% ACN, 15% H$_2$O) at λ=214 nm using a hypersil column from National Scientific (250× 4.6 mm) at 40° C. and only fractions higher than 95% purity were combined. [M+H]$^+$ calcd for C$_{62}$H$_{99}$N$_{14}$O$_{21}$, 1375.7; found 1375.7.

6.1.5 Synthesis of Additional Dab$^9$ Derivatives

Additional derivatives as specified in TABLE 1 were also synthesized. All acylations of aspartocin with amino acids were performed on 50 mg of aspartocin complex and the same ratio of the reagents as noted in Section 6.1.1, supra. In cases where the amino acid carries a t-butyl based protecting group, such as Fmoc-Ser(t-Bu)-OH, after removal of Fmoc, trifluoroacetic acid (2 mL) was added and the mixture was stirred overnight. The mixture was then filtered as described before and purified by prep HPLC.

6.1.6 Purification of the Dab$^9$ Derivatives

In general, the various Dab$^9$ derivatives of aspartocin have very similar retention times on prep as well as on analytical HPLC. On prep, most derivatives eluted at about 28 to 30 minutes and on analytical at about 13 to 14 minutes. Each fraction was tested by analytical HPLC for purity as well as by ion spray mass spectrometry for characterization. The natural product produced by fermentation contains a family of analogs of aspartocin with the C$_{15}$ fatty acid as the most abundant compound and the C$_{14}$ fatty acid as the second abundant compound, in addition to other analogs. The C$_{14}$ and C$_{15}$ fatty acid fractions were separated by prep HPLC as described in Section 6.1.2, supra, and submitted for MIC measurements as described below. The various compounds synthesized and tested, as well as their observed masses (M+H) as determined by mass spectrometry, are provided in TABLE 1.

6.2 In Vitro Antimicrobial Activity

This Example demonstrates that the various Dab$^9$ aspartocin derivatives synthesized according to the previous example exhibit significant antimicrobial activity against Gram-positive bacteria in in vitro assays.

6.2.1 Determination of MIC

Minimum Inhibitory Concentrations (MICs) were determined in the presence and absence of calcium according to the protocol described in Approved Standard M7-A3, supra. For measurements carried out in the presence of calcium, 4 mM CaCl$_2$ was added to the media at the beginning of the assay.

6.2.2 Results

The results of the various assays are tabulated in TABLE 1, below. As can be seen from TABLE 1, the presence of primary and secondary amines spaced about 3-6 carbons from the Dab$^9$ β-amine improves the activity of these antimicrobial compounds. Amino acid side chains are well tolerated and do not appear to decrease the antimicrobial activity of the compounds.

TABLE 1

| Compound | | MIC (μg/mL)[1] | | | Mass | |
| No. | Name | w/Ca$^{2+}$ | w/o Ca$^{2+}$ | ED$_{50}$ | Calcd | Observed (M + H) |
| --- | --- | --- | --- | --- | --- | --- |
| IB-756 | Aspartocin | 2 | 1 | 3 | | |
| IB-1272 | NatC$_{15}$-aspartocin(Dab$^9$-N-glycyl) | 0.8 | 0.7 | 1.8 | 1374.7 | 1375.7 |
| IB-1274 | NatC$_{14}$-aspartocin(Dab$^9$-N-L-alanyl) | 32 | 2 | | 1374.7 | 1375.8 |
| IB-1275 | NatC$_{15}$-aspartocin(Dab$^9$-N-L-alanyl) | 16 | 1 | 15.7 | 1388.7 | 1389.8 |
| IB-1278 | NatC$_{15}$-aspartocin(Dab$^9$-N-β-alanyl) | 2 | 2 | | 1388.7 | 1389.8 |
| IB-1279 | NatC$_{15}$-aspartocin(Dab$^9$-N-D-alanyl) | 2 | 1 | 6 | 1388.7 | 1389.8 |
| IB-1280 | NatC$_{14}$-aspartocin(Dab$^9$-N-D-alanyl) | 4 | 0.5 | | 1374.7 | 1375.8 |
| IB-1281 | NatC$_{15}$-aspartocin(Dab$^9$-N-L-seryl) | 16 | 1 | 14.7 | 1404.7 | 1405.8 |
| IB-1282 | NatC$_{15}$-aspartocin(Dab$^9$-N-L-lysyl) | 8 | 0.5 | | 1445.8 | 1446.8 |
| IB-1303 | NatC$_{15}$-aspartocin(Dab$^9$-N-scarcosyl) | 1 | 1.3 | | 1388.7 | 1389.7 |
| IB-1305 | NatC$_{14}$-aspartocin(Dab$^9$-N-γ-aminobutyryl) | | | | 1388.7 | 1389.7 |
| IB-1307 | NatC$_{15}$-aspartocin(Dab$^9$-N-γ-aminobutyryl) | 2 | 0.5 | | 1402.7 | 1403.7 |
| IB-1308 | NatC$_{15}$-aspartocin (Dab$^9$-N-glycyl) | 2 | 2 | | 1360.7 | 1361.7 |
| IB-1312 | NatC$_{15}$-aspartocin (Dab$^9$-N-histidyl) | 10.7 | 1.7 | | 1459.7 | 1455.7 |

[1]All MICs are the average of three datapoints.

6.3 In Vivo Efficacy

The in vivo efficacy of the compounds of the invention was demonstrated with compound 1272 in a mouse protection model.

6.3.1 Protocol

6.3.1.1 Preparation of Inoculum

An overnight culture of methicillin sensitive *Staphylococcus aureus* ("MSSA"; Smith strain) grown to stationary phase in brain heart infusion broth (BHI) was diluted 1000-fold and maintained at 37° C. in a shaking incubator. Approximately two hours later the culture was centrifuged and the pellet was washed with sterile phosphate-buffered saline ("PBS"). The washed pellet was then reconstituted in Mueller-Hinton Broth ("MHB") to achieve the desired density of bacteria. A portion of the inoculum was plated on blood agar plates to determine colony-forming units (CFU) per milliliter.

6.3.1.2 Formulation

Compound IB-1272 was formulated immediately before dosing in aqueous vehicle containing 5% dextrose. Compound IB-756 (Aspartocin) was formulated in PBS or 5% dextrose and used as a positive control.

6.3.1.3 Regimen

Immunocompetent Swiss Webster mice from Simonsen Laboratories, Gilroy, Calif., received via intraperitoneal injection a single inoculum (0.5 ml) containing an estimated $4.0 \times 10^7$ CFU of MSSA Smith strain. The day of inoculation was designated study day 0. Immediately after infection, mice were treated subcutaneously with a single dose of vehicle alone, IB-1272 (2, 4, or 8 mg/kg), IB-756 (2.5 or 5 mg/kg in PBS), or IB-756 (2.5 or 5 mg/kg in 5% dextrose). A detailed description of the group assignments is presented in TABLE 2.

TABLE 2

| Group | Predicted CFU/mouse | Actual CFU/mouse[a] | Number of Mice | Test Article | Conc. (mg/ml) | Dose Volume (ml/kg) | Dosage (mg/kg) |
|---|---|---|---|---|---|---|---|
| 1 | $4.0 \times 10^7$ | $3.56 \times 10^7$ | 11 | Vehicle | 0 | 4 | 0 |
| 2 | $4.0 \times 10^7$ | $3.56 \times 10^7$ | 10 | IB-756 (in PBS) | 0.63 | 4 | 2.5 |
| 3 | $4.0 \times 10^7$ | $3.56 \times 10^7$ | 10 | IB-756 (in PBS) | 1.25 | 4 | 5.0 |
| 4 | $4.0 \times 10^7$ | $3.56 \times 10^7$ | 10 | IB-756 (in 5% dextrose) | 0.63 | 4 | 2.5 |
| 5 | $4.0 \times 10^7$ | $3.56 \times 10^7$ | 10 | IB-756 (in 5% dextrose) | 1.25 | 4 | 5.0 |
| 6 | $4.0 \times 10^7$ | $3.56 \times 10^7$ | 10 | IB-1272 | 0.5 | 4 | 2.0 |
| 7 | $4.0 \times 10^7$ | $3.56 \times 10^7$ | 10 | IB-1272 | 1.0 | 4 | 4 |
| 8 | $4.0 \times 10^7$ | $3.56 \times 10^7$ | 10 | IB-1272 | 2.0 | 4 | 8 |

[a] Actual CFU obtained from plate counts of the inoculum.

6.3.2 Results

Survival data are summarized in TABLE 3. Mortality in the vehicle-control mice was 100%. Mortality among mice treated subcutaneously with IB-756 (formulated in PBS) at doses of 2.5 or 5 mg/kg was 60% and 0%, respectively. Mortality among mice treated subcutaneously with IB-756 (formulated in 5% dextrose) at doses of 2.5 or 5 mg/kg was 50% and 0%, respectively. Mortality among mice treated subcutaneously with IB-1272 at doses of 2, 4, or 8 mg/kg was 50%, 0% and 0%, respectively.

The $ED_{50}$ for subcutaneously administered IB-1272 was <2.0 mg/kg in immunocompetent mice challenged intraperitoneally with MSSA Smith strain. The efficacy of IB-756 (aspartocin) was the same when formulated in 5% dextrose or in PBS.

TABLE 3

Survival of Immunocompetent Mice infected Intraperitoneally with MSSA and Dosed Subcutaneously with IB-1272

| Group | Compound | Actual CFU/Mouse | Dosage (mg/kg) | Number of Mice | Number Dead | Percent Mortality | Percent Survival |
|---|---|---|---|---|---|---|---|
| 1 | None | $3.56 \times 10^7$ | 0 (vehicle) | 11 | 11 | 100 | 0 |
| 2 | IB-756 (in PBS) | $3.56 \times 10^7$ | 2.5 | 10 | 6 | 60 | 40 |
| 3 | IB-756 (in PBS) | $3.56 \times 10^7$ | 5.0 | 10 | 0 | 0 | 100 |
| 4 | IB-756 (in 5% dextrose) | $3.56 \times 10^7$ | 2.5 | 10 | 5 | 50 | 50 |
| 5 | IB-756 (in 5% dextrose) | $3.56 \times 10^7$ | 5.0 | 10 | 0 | 0 | 100 |
| 6 | IB-1272 | $3.56 \times 10^7$ | 2.0 | 10 | 5 | 50 | 50 |
| 7 | IB-1272 | $3.56 \times 10^7$ | 4 | 10 | 0 | 0 | 100 |
| 8 | IB-1272 | $3.56 \times 10^7$ | 8 | 10 | 0 | 0 | 100 |

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

We claim:

1. A compound having the formula:

wherein R is $R^1$ is selected from $(C_1-C_{25})$ alkyl, $(C_1-C_{25})$ alkyl substituted with one or more of the same or different $R^{15}$ groups, $(C_1-C_{25})$ heteroalkyl, $(C_1-C_{25})$ heteroalkyl substituted with one or more of the same or different $R^{15}$ groups, $(C_5-C_{10})$ aryl, $(C_5-C_{10})$ aryl substituted with one or more of the same or different $R^{15}$ groups, $(C_5-C_{15})$ arylaryl, $(C_5-C_{15})$ arylaryl substituted with one or more of the same or different $R^{15}$ groups, $(C_5-C_{15})$ biaryl, $(C_5-C_{15})$ biaryl substituted with one or more of the same or different $R^{15}$ groups, 5-10 membered heteroaryl, 5-10 membered heteroaryl substituted with one or more of the same or different $R^{15}$ groups, $(C_6-C_{26})$ arylalkyl, $(C_6-C_{26})$ arylalkyl substituted with one or more of the same or different $R^{15}$ groups, 6-26 membered heteroarylalkyl, and 6-26 membered heteroarylalkyl substituted with one or more of the same or different $R^{15}$ groups;

each $R^{15}$ is independently selected from —$OR^{16}$, —$SR^{16}$, —$NR^{16}R^{16}$, —CN, —$NO_2$, —$N_3$, —C(O)$OR^{16}$, —C(O)$NR^{16}R^{16}$, —C(S)$NR^{16}R^{16}$, —C($NR^{16}$)$NR^{16}R^{16}$, —CHO, —$R^{16}$CO, —$SO_2R^{16}$, —$SOR^{16}$, —PO($OR^{16}$)$_2$, —PO($OR^{16}$), —$CO_2H$, —$SO_3H$, —$PO_3H$, halogen, and trihalomethyl;

each $R^{16}$ is independently selected from hydrogen, $(C_1-C_6)$ alkyl, $(C_5-C_{10})$ aryl, 5-10 membered heteroaryl, $(C_6-C_{16})$ arylalkyl, and 6-16 membered heteroarylalkyl;

$R^2$ is OH or $NH_2$;

PG is a protecting group; and $R^{6'}$ is independently selected from at least one amino acid, —X—$R^{10}$—$NR^7$—, and —X—$(CR^{11}R^{11})_n$—$NR^7$—, wherein:

X is —C(O)—, —C(O)O—, —C(NH)—, or —S(O)$_2$—;

$R^7$ is hydrogen or $(C_1-C_4)$ alkyl;

$R^{10}$ is independently selected from —$CH_2$—, —CH═CH—, —C≡C—, —O—, —S—, —NH—, —NH—NH—, —N═N—, —C(O)—, —S(O)$_2$—, —S(O)$_2$—O—, —C(NH)—, $(C_1-C_6)$ alkyldiyl, $(C_1-C_6)$ alkyleno, and $(C_1-C_6)$ alkano, wherein $R^{10}$ is optionally substituted with —$NR^8R^8$, —$OR^8$, —$SR^8$, halogen, trihalomethyl, —CN, —C(O)$R^8$, —C(O)$OR^8$, —C(O)$NR^8R^8$, amidine, guanidine, alkyl optionally substituted with one or more of the same or different $R^9$, aryl optionally substituted with one or more of the same or different $R^9$, arylalkyl optionally substituted with one or more of the same or different $R^9$, heteroalkyl optionally substituted with one or more of the same or different $R^9$, and heteroarylalkyl optionally substituted with one or more of the same or different $R^9$;

each $R^8$ is independently selected from hydrogen, alkyl, aryl, arylalkyl, heteroaryl and heteroarylalkyl; and each $R^9$ is independently selected from —$NR^8R^8$, —$OR^8$, —$SR^8$, halogen, trihalomethyl, —CN, —C(O)$R^8$, —C(O)$OR^8$, —C(O)$NR^8R^8$, amidine, guanidine, alkyl, aryl, arylalkyl, heteroaryl, and heteroarylalkyl;

each $R^{11}$ is independently selected from hydrogen, amino, amido, amidino, carboxy, guandino, hydroxy, sulfanyl, $(C_1-C_4)$ alkyl, $(C_1-C_4)$ alkyl substituted with one or more of the same or different $R^{12}$, $(C_5-C_{10})$ aryl, $(C_5-C_{10})$ aryl substituted with one or more of the same or different $R^{12}$, $(C_6-C_{13})$ arylalkyl, $(C_6-C_{13})$ arylalkyl substituted with one or more of the same or different $R^{12}$, 5-10 membered heteroaryl, 5-10 membered heteroaryl substituted with one or more of the same or different $R^{12}$, 6-13 membered heteroarylalkyl, and 6-13 membered heteroarylalkyl substituted with one or more of the same or different $R^{12}$;

each $R^{12}$ is independently selected from amino, amido, amidino, carboxyl, guanidino, hydroxy, and sulfanyl;

n is an integer from 1 to 6.

2. The compound of claim 1, wherein $R^{6'}$ is —X—$R^{10}$—$NR^7$— or —X—$(CR^{11}R^{11})_n$—$NR^7$— and X is —C(O)—.

3. The compound of claim 1, wherein $R^{6'}$ comprises an amino acid.

4. The compound of claim 3, wherein $R^{6'}$ is an amino acid.

5. The compound of claim 4, wherein $R^{6'}$ is β-alanyl.

6. A method of making the compound of claim 1, the method comprising:

a) reacting a compound having the formula (A)

(A)

to add —$R^{6'}$—PG to form the compound of claim 1.

7. The compound of claim 1, wherein the protecting group PG is tert-butyloxycarbonyl, 9-fluorenylmethoxycarbonyl, or benzyloxycarbonyl.

8. The compound of claim 7, wherein PG is 9-fluorenyl-methoxycarbonyl.

* * * * *

UNITED STATES PATENT AND TRADEMARK OFFICE
CERTIFICATE OF CORRECTION

| | | |
|---|---|---|
| PATENT NO. | : 7,655,623 B2 | Page 1 of 1 |
| APPLICATION NO. | : 11/539139 | |
| DATED | : February 2, 2010 | |
| INVENTOR(S) | : Fardis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 169 days.

Signed and Sealed this

Twenty-eighth Day of December, 2010

David J. Kappos
*Director of the United States Patent and Trademark Office*